US006987566B1

(12) United States Patent
Smith

(10) Patent No.: US 6,987,566 B1
(45) Date of Patent: Jan. 17, 2006

(54) METHODS AND APPARATUS FOR ANALYZING MIRROR REFLECTANCE

(75) Inventor: David S. Smith, Fort Wayne, IN (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 422 days.

(21) Appl. No.: 10/304,768

(22) Filed: Nov. 27, 2002

(51) Int. Cl.
*G01J 4/00* (2006.01)
(52) U.S. Cl. ........................... 356/369; 356/364
(58) Field of Classification Search ......... 356/364–369
See application file for complete search history.

(56) References Cited

U.S. PATENT DOCUMENTS

| 4,171,910 | A | | 10/1979 | Derderian et al. |
| 4,786,169 | A | | 11/1988 | Brierley et al. |
| 5,220,397 | A | * | 6/1993 | Huang et al. ............... 356/140 |
| RE34,783 | E | | 11/1994 | Coates |
| 5,486,701 | A | | 1/1996 | Norton et al. |
| 5,726,455 | A | | 3/1998 | Vurens |
| 5,898,181 | A | | 4/1999 | Vurens |
| 6,075,612 | A | | 6/2000 | Mandella et al. |
| 6,088,117 | A | | 7/2000 | Imura et al. |
| 6,134,011 | A | | 10/2000 | Klein et al. |
| 6,307,627 | B1 | | 10/2001 | Vurens |
| 6,327,040 | B2 | | 12/2001 | Thakur et al. |
| 2002/0071118 | A1 | * | 6/2002 | Shinbori et al. ............ 356/326 |
| 2002/0191092 | A1 | * | 12/2002 | Hayashi et al. ............. 348/294 |
| 2003/0155489 | A1 | * | 8/2003 | Yasuda et al. .............. 250/225 |

OTHER PUBLICATIONS

David S. Smith; "Scan-Angle Analysis for Remote Sensing Instrument Mirrors" Sep. 20, 2000; pp. 1-20.

* cited by examiner

*Primary Examiner*—Michael P. Stafira
(74) *Attorney, Agent, or Firm*—Edell, Shapiro & Finnan, LLC

(57) ABSTRACT

Methods and apparatus are described for assessing the reflective properties of mirrors at different angles of incidence without precise knowledge of the mirror's basic optical constants and/or without precise knowledge of the mirror's over-coating prescription. Reflectance values can be accurately calculated for multiple angles of incidence based upon measurement data collected for a single angle of incidence. The approach uses equations based on the Fresnel equations for reflectance in which reflectance is calculated as a function of the angle of incidence of incoming light to the scanned mirror used to collect the signal. The angle of incidence-based approach allows accurate reflectance values to be calculated over a broad range of wavelengths and angle of incidences without detailed knowledge of the optical properties of the coating material and the substrate underneath. The described methods and apparatus are particularly useful for calibrating measurements made with remote sensing instruments that use scanned mirrors.

36 Claims, 12 Drawing Sheets

METHODS AND APPARATUS FOR ANALYZING MIRROR REFLECTANCE

BACKGROUND OF THE INVENTION

1. Field of the Invention

The invention relates to methods and apparatus for assessing the reflective properties of mirrors at different angles of incidence without precise knowledge of the mirror's basic optical constants and/or without precise knowledge of the mirror's over-coating prescription. More particularly, the invention relates to accurately estimating reflectance values for multiple angles of incidence based upon measured reflectance values collected for a single or a few angles of incidence.

2. Description of the Related Art

Many remote sensing instruments make use of mirrors that scan over a wide range of angles to produce a large field-of-view image, such as those images typically taken by satellites of the earth, or images taken by optical telescopes of distant planets and galaxies. While this approach is simple in concept, a significant complication is that the reflectance of a scanning mirror varies, depending upon the angle at which light strikes the mirror (i.e., the "angle of incidence" of the incoming light). This angle of incidence of incoming light is typically measured as an angle relative to a perpendicular to the surface of the mirror at the point of incidence.

A further complication is that the reflectance of the S-polarization and P-polarization components of light at a particular wavelength vary differently as the angle of incidence changes. Unless corrections are made to account for the changes in a scanning mirror's S-polarization reflectance and P-polarization reflectance as a function of the angle of incidence, the uncorrected changes will decrease the calibration accuracy of the remote sensing instrument's output measurements. As a consequence, it is necessary to produce a calibration equation that accurately includes a model of the instrument's response as a function of angle of incidence. Such a model is preferably based on a theoretical mathematical model of the underlying physical reflectance phenomenon, or, if that is not possible, a combination of a physical model and measured reflectance values.

For most remote sensing mirrors, calibration uncertainties associated with scan mirror reflectance are made more serious by the use of absorbing coatings on the mirror surfaces to protect them from damage. While these coatings provide protection from damage, they also change the angular dependence of the reflectance of the mirror, particularly in some key wavelength ranges of the IR spectrum. If the optical constants of the substrate and the over-coating are accurately known, reflectance of the mirror at different angles of incidence is easily calculated using the basic Fresnel equations. The difficulty for instrument manufacturers is that the over-coating prescription is not necessarily known (e.g., proprietary coatings are used) or the manufacturing and storage process may not be controlled well enough to allow accurate calculation of the reflectance from basic optical constants of the deposited protective material. Furthermore, the optical qualities of over-coatings can change over time, due to prolonged exposure to extreme conditions, requiring that the reflectivity of a mirror be periodically reassessed for recalibration purposes.

Devices that use a scanning mirror to take measurements typically adjust individual measurements made by the device to accommodate variances in the reflectance of the scanning mirror for the wavelength and specific angle of incidence at which the measurement was made. To assure maximum accuracy of measurements the reflective properties of the mirror at different angles of incidence are, preferably, periodically recalculated. There are several ways in which such calibration/recalibration can be achieved.

First, with knowledge of the indices of refraction (n) and the absorption coefficients (k) of the coated mirror layers, the Fresnel reflectance equations can be used as a physical model to calculate expected reflectance values. However, values of n and k vary widely as a function of the wavelength of the light ($\lambda$) and the details of the mirror coating process. Therefore, calculated reflectance values are preferably compared against measured reflectance values to enhance confidence and/or to develop linear scaling factors to accommodate external or unknown physical effects not represented in the Fresnel equations. Once validated, the corrected Fresnel equations can be used to extrapolate highly accurate reflectance values. However, as previously discussed, this approach is typically hindered by a lack of information with respect to proprietary mirror coatings, and/or changes in optical characteristics due to environmental effects.

As a second approach, a set of reflectance values are physically measured at a specific wavelength and used to develop a polynomial equation that "fits" the measured mirror reflectance values as a function of angle of incidence for each wavelength. The polynomial equation developed for each wavelength can then be used as the model/algorithm for calculating the angle of incidence effect on instrument throughput for the wavelength so modeled. Although such polynomial equations are able to fit measured reflectance values to a rather high degree of precision, a polynomial equation is not based upon a mathematical model of the physical phenomenon of mirror reflectance. Therefore, a polynomial equation does not fundamentally provide a true representation of the expected behavior of the mirror as a function of angle of incidence. The polynomial equation merely connects the measured reflectance values irrespective of whether the measured reflectance values contain errors. Values of reflectance calculated using such a polynomial equation will, therefore, inherently integrate previous measurement errors. Errors in the measured reflectance values to which the polynomial equation is fitted will not be detected, and reflectance values calculated using the resulting polynomial equation will be consistent with the original faulty reflectance value measurements.

Another deficiency associated with the use of polynomial equations to model mirror reflectance is that the approach requires a significant number of manual measurements of mirror reflectance versus angle of incidence so that an accurate polynomial equation can be developed that matches the resulting measured reflectance values. Such measurements must be taken for each wavelength with which the mirror will be used, because previously developed polynomial equations are not based upon a physical model and, therefore, cannot be accurately relied upon to predict reflectivity of the mirror at other wavelengths.

In a third approach, a large number of physical measurements are made and stored in one or more lookup tables. Reflectance measurements must be made for each angle of incidence/wavelength combination at which the scan mirror is used. Interpolation is then used to extrapolate values between measured points. Although simple in concept, such an approach requires a large number of measured reflectance value data points and sufficient storage capacity to support use of the technique. Recalibration of devices that use such a technique requires taking an entirely new set of reflectance value measurements, specific to each individual device.

While all three approaches can be used to extrapolate the reflectance values of a coated mirror in a laboratory (i.e., with the assistance of special test equipment and special test configurations), all three approaches suffer from serious deficiencies with respect to their ability to be adapted for use in deployed devices (i.e., outside of a controlled laboratory environment in which specialized support equipment and personnel are not readily available). Furthermore, these approaches cannot be used to develop high confidence reflectance values at multiple angles of incidence based upon reflectance values measured at one or a few angles of incidence, thereby significantly increasing the number of measured reflectance values required to facilitate generation of accurate reflectance values across multiple angles of incidence. Such deficiencies are further exacerbated in remote sensing devices deployed into orbit around the earth or deployed to the far reaches of outer-space. Such devices are, typically, constrained in size, weight and design and are inaccessible to technicians with the required calibration equipment.

Hence, there is a need for methods and apparatus capable of accurately estimating the angular dependence of reflectivity of a coated mirror across a broad spectrum of wavelengths while based upon a reduced number of manual measurements and without precise knowledge of the mirror's basic optical constants and/or without precise knowledge of the mirror's over-coating prescription. The new methods and apparatus should integrate physical models of the angular dependence of mirror reflectance that can be used to validate reflectivity measurements of a mirror at different angles of incidence and wavelengths despite variances in the refraction and absorption qualities of the mirror's protective coating. The novel methods and apparatus should simplify present physical reflectance models so that accurate reflectance values can be quickly and efficiently extrapolated, so that errors associated with measured mirror reflectance values at different angles of incidence can be quickly identified, and measurements made from light reflected by a scanning mirror can be readily corrected.

SUMMARY OF THE INVENTION

Therefore, in light of the above, and for other reasons that will become apparent when the invention is fully described, an object of the invention is to estimate the reflectivity of a mirror at angles of incidence based upon knowledge of the mirror's reflectance at a reference angle of incidence.

Another object of the invention is to reduce the number of manual measurements required to ascertain the reflectivity of a mirror at different angles of incidence left unmeasured across a broad spectrum of wavelengths.

Yet another object of the invention is to predict and validate the variation of the reflectivity of a mirror at different angles of incidence despite variances in the refraction and absorption qualities of the mirror's protective coating.

A further object of the invention is to quickly determine the quality of mirror reflectance values and to identify, assess, and estimate errors and resultant calibration uncertainties associated with variation of mirror reflectance values at different angles of incidence.

A still further object of the invention is provide reflectance values over a broad range of wavelengths and at different angles of incidence to support accurate correction of signal measurements received via a scanning mirror.

It is yet a further object of the invention to efficiently and accurately assess reflectance characteristics for scanning mirrors within a controlled laboratory environment as well as for scanning mirrors integrated within remote sensing equipment.

The aforesaid objects are achieved individually and in combination, and it is not intended that the invention be construed as requiring two or more of the objects to be combined unless expressly required by the claims attached hereto.

Methods and apparatus are described for assessing the reflective properties of mirrors at different angles of incidence without precise knowledge of the mirror's basic optical constants and/or without precise knowledge of the mirror's over-coating prescription. Reflectance values are accurately calculated for multiple angles of incidence based upon measurement data collected for one, or several, angles of incidence.

Embodiments of the invention relate to a method and apparatus for determining the reflectance of a mirror as a function of angle of incidence, in which the P-polarization and S-polarization reflectance of the mirror at a particular angle of incidence (reference angle of incidence) relative to the normal of a reflective surface of the mirror is measured. Furthermore, S-polarization and P-polarization reflectance over a range of angles of incidence is calculated based upon measured S-polarization and P-polarization reflectance values acquired at the reference angle of incidence.

The approach uses equations based on the Fresnel equations (but not directly derived) for reflectance in which reflectance is calculated as a function of the angle of incidence of incoming light to the scanned mirror used to collect the signal. The angle of incidence-based approach allows accurate relative reflectance values to be calculated over a broad range of wavelengths and angles of incidence without detailed knowledge of the optical properties of the coating material and the substrate underneath.

Calculations using the angle of incidence-based exponential equations are facilitated by substituting measured values for the S-polarization reflectance of the mirror measured at the reference angle of incidence as an approximation of the P-polarization reflectance at normal incidence. Calculations using the angle of incidence-based exponential equations are further facilitated by assuming that the value of alpha ($\alpha(\lambda)$) calculated for a reference angle of incidence at a specific wavelength is constant across a range of angles of incidence. Methods and techniques are described by which the range of angles of incidence, over which $\alpha(\lambda)$ can be assumed to be constant, is determined. Furthermore, methods and techniques are described by which reflectance values calculated using the incidence-based exponential equations are scaled to match sampled measurements and thereby accommodate device characteristics and physical effects not accounted for in the Fresnel equations.

By repeating the methods and techniques described for a set of reference angles of incidence across a set of reference wavelengths, accurate reflectance calculations can be made that provide complete coverage of a desired range of angles of incidence, for an identified spectrum. The methods and techniques described are particularly useful for calibrating measurements made with remote sensing instruments that use scanned mirrors because more accurate corrections can be made while the need for physical measurements is minimized.

The above and still further objects, features and advantages of the invention will become apparent upon consideration of the following descriptions and descriptive figures of specific embodiments thereof. While these descriptions go into specific details of the invention, it should be understood

DETAILED DESCRIPTION OF THE PREFERRED EMBODIMENTS

Figure 1:
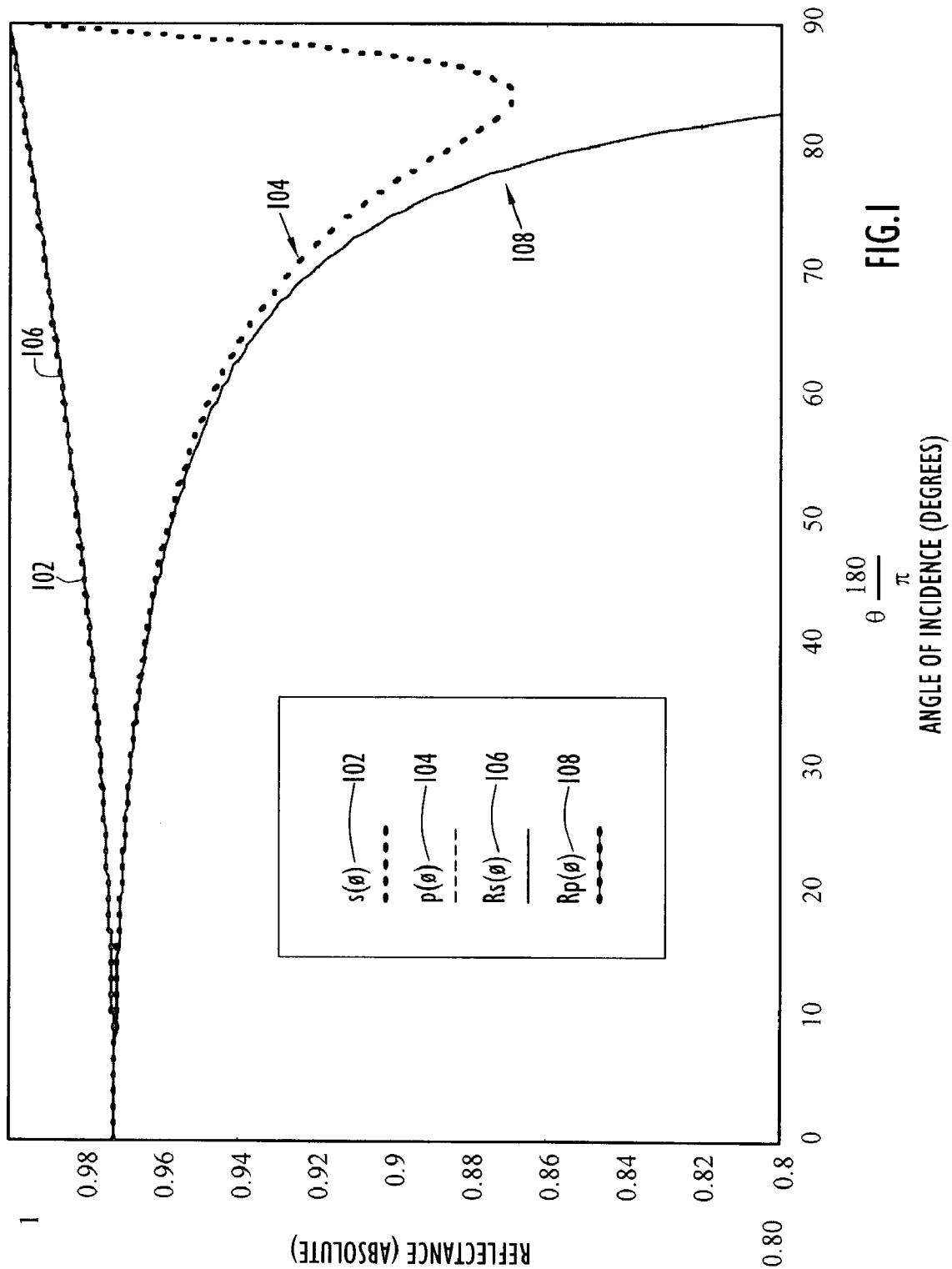
FIG. 1 is a data chart that presents two representative sets of calculated S-polarization reflectance values and P-polarization reflectance values (for light at a single wavelength) versus angle of incidence: the first set of S-polarization reflectance values and P-polarization reflectance values calculated using Fresnel's reflectance equations; the second set of S-polarization reflectance values and P-polarization reflectance values calculated using a simplified version of Fresnel's reflectance equations based upon angle of incidence, in accordance with an exemplary embodiment of the invention.

Preferred embodiments according to the present invention are described below with reference to the above drawings, in which like reference numerals designate like components.

The Fresnel reflection from smooth metal surfaces is a well-understood and highly characterized phenomenon. Light at a single wavelength can be characterized by an S-polarization vector and a P-polarization vector. The S-polarization electric vector is always parallel to the mirror surface (by definition in the measurement setup context), resulting in very little effect of angle of incidence on that polarization. However, the P-polarization vector can be significantly affected by angle of incidence. Approximate Fresnel reflectance equations for S-polarization and P-polarization as a function of angle from a smooth metal surface are given by:

$$R_P = \frac{(n^2 + k^2)\cos^2\theta - 2n\cos\theta + 1}{(n^2 + k^2)\cos^2\theta + 2n\cos\theta + 1} \tag{1}$$

and, $$R_S = \frac{(n^2 + k^2) - 2n\cos^2\theta + \cos^2\theta}{(n^2 + k^2) + 2n\cos^2\theta + \cos^2\theta} \tag{2}$$

The index of refraction, n, and absorption coefficient, k, are familiar optical constants of the metal, and $\theta$ is the angle of incidence measured relative to the surface normal. Dependence of n and k on wavelength, $\lambda$, can vary rapidly in the absorption regions of some protective coatings used on remote mirrors. These equations hold accurately only when $n^2+k^2 \gg 1$. A further simplification of the equation for $R_p$ can be made using the following expression:

$$R_p(\lambda) = R_0(\lambda) e^{-\alpha(\lambda)(\sec(\theta)-1)} \tag{3}$$

where $R_0(\lambda)$ is the reflectance at normal incidence and is given by $$R_0(\lambda) = \frac{[n(\lambda) - 1]^2 + k(\lambda)^2}{[n(\lambda) + 1]^2 + k(\lambda)^2} \tag{4}$$

and α(λ) is given by the following:

$$\alpha(\lambda) = \frac{4n(\lambda)}{n(\lambda)^2 + k(\lambda)^2} \quad (5)$$

S-polarization reflectance can be approximated by a similar expression:

$$R_s(\lambda) = R_0(\lambda) e^{-\alpha(\lambda)(\cos(\theta)-1)} \quad (6)$$

FIG. 1 presents a comparison of two approximations of the Fresnel equations for reflectance (at a single wavelength) as a function of angle of incidence. The dotted lines (for both S-polarization reflectance values 102 and P-polarization reflectance values 104) were calculated using the Fresnel reflectance equations (i.e., using Equation (1) and Equation (2)) for a reflective surface of known refraction (n) and absorption coefficient (k) values. The solid lines (for both S-polarization reflectance values 106 and P-polarization reflectance values 108) were calculated using the angle of incidence-based exponential equations (i.e., Equation (6) and Equation (3), respectively), presented above, based on angle of incidence. The reason for creating the angle of incidence-based exponential equations depicted in Equation (3) and Equation (6), is to provide a Fresnel based model (i.e., a physical model) that is not dependent upon the values of refraction (n) and absorption coefficient (k) values. Solving equation 3 for α(λ) yields:

$$\alpha(\lambda) = \frac{\ln[R_P(\lambda)/R_0(\lambda)]}{1 - \sec(\theta)} \quad (7)$$

By using Equation (7) to calculate an α(λ) for each wavelength of a measured curve of reflectance versus wavelength at any one angle of incidence, one is able to calculate approximations of S-polarization reflectance and P-polarization reflectance at other angles of incidence using Equation (3) and Equation (6), respectively. For example, using Equation (3) and a measurement-based α(λ), one can estimate P-polarization reflectance at other angles of incidence even though the optical constants (i.e., the n and k values) for the coatings are unknown.

FIGS. 2 through 11 illustrate the use and effectiveness of the above-described techniques with respect to two representative scanning mirror samples. The first mirror sample, and representative reflectance values, is associated with a portion of a scanning mirror from a Geostationary Operational Environmental Satellite (GOES). The second mirror sample, and representative reflectance values, is associated with a portion of a scanning mirror from a Moderate Resolution Imaging Spectroradiometer (MODIS).

Figure 2:
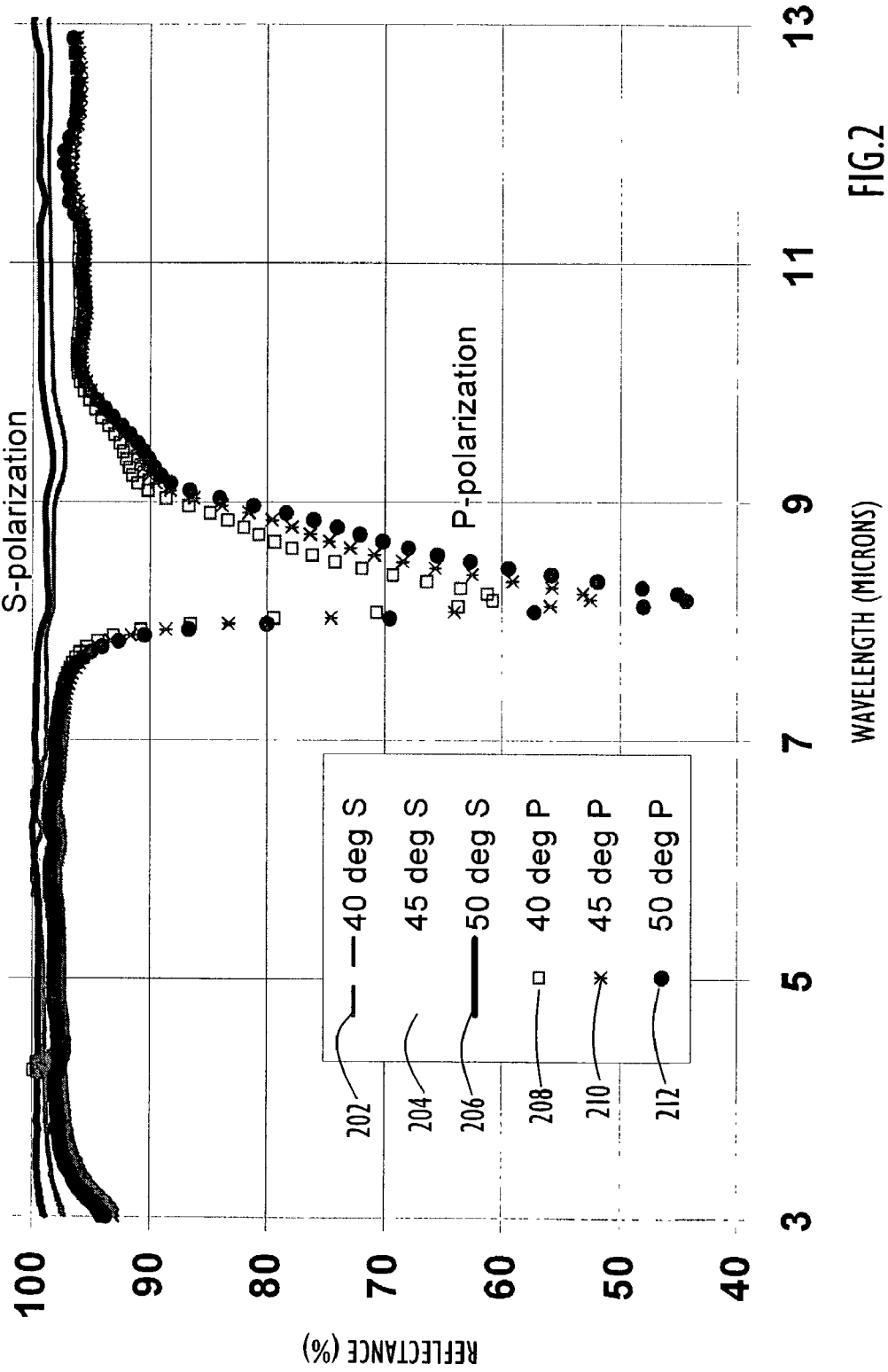
FIG. 2 is a data chart that presents measured S-polarization reflectance values and P-polarization reflectance values versus wavelength for three angles of incidence (i.e., 40°, 45°, and 50°) for a mirror sample representative of that used by a Geostationary Operational Environmental Satellite (GOES).

FIG. 2 is a data chart that presents measured S-polarization reflectance values and P-polarization reflectance values versus wavelength for three angles of incidence (i.e., 40°, 45°, and 50°) for the GOES mirror sample. The mirror is made of an enhanced aluminum with an $SiO_x$ over coating to protect the aluminum from degradation. A side effect of the protective layer is that polarization of the reflected light depends on wavelength and angle of incidence.

As depicted in FIG. 2, S-polarization reflectance values for an angle of incidence of 40° are shown at 202, S-polarization reflectance values for an angle of incidence of 45° are shown at 204, and S-polarization reflectance values for an angle of incidence of 50° are shown at 206. However, the S-polarization reflectance values for all three measured angles are near 100%, and virtually wavelength independent, therefore, lines 202, 204, and 206, as shown in FIG. 2, highly overlap. Also depicted in FIG. 2, are P-polarization reflectance values for an angle of incidence of 40° at 208, for an angle of incidence of 45° at 210, and for an angle of incidence of 50° at 212. P-polarization reflectance values vary significantly at certain wavelengths.

S-polarization reflectance measurements depicted in FIG. 2 are consistent with S-polarization reflectance curves calculated for a single wavelength across multiple angles of incidence as depicted in FIG. 1. For example, as shown in FIG. 1, the S-polarization reflectance for at least one representative highly reflective surface (i.e., a surface with $n^2+k^2>>1$) can be expected to vary less than 3% over angles of incidence between 0° and 90°.

The reason that such results can be expected is that the S-polarization electric vector is always parallel to the mirror surface resulting in very little effect of angle of incidence on that polarization. In fact, at 0° incidence both S-polarization reflectance and P-polarization reflectance must be the same, and in the case of highly reflective surfaces, such as an aluminum mirror, the normal angle reflectance is very high. In fact, as shown in FIG. 1, for highly reflective surfaces (i.e., in which $n^2+k^2>>1$) the S-polarization reflectance should be very nearly the same as the P-polarization reflectance at normal incidence. As will be described in greater detail, based upon this fact, measured reflectance values for the S-polarization at normal incidence can be substituted for (and also used to validate measurements of P-Polarization reflectance) the P-polarization at normal incidence (i.e., $R_0$). This greatly facilitates calculations made using Equation (3), Equation (6), and Equation (7) and analysis of P-polarization reflectance as a function of angle of incidence.

Figure 3:
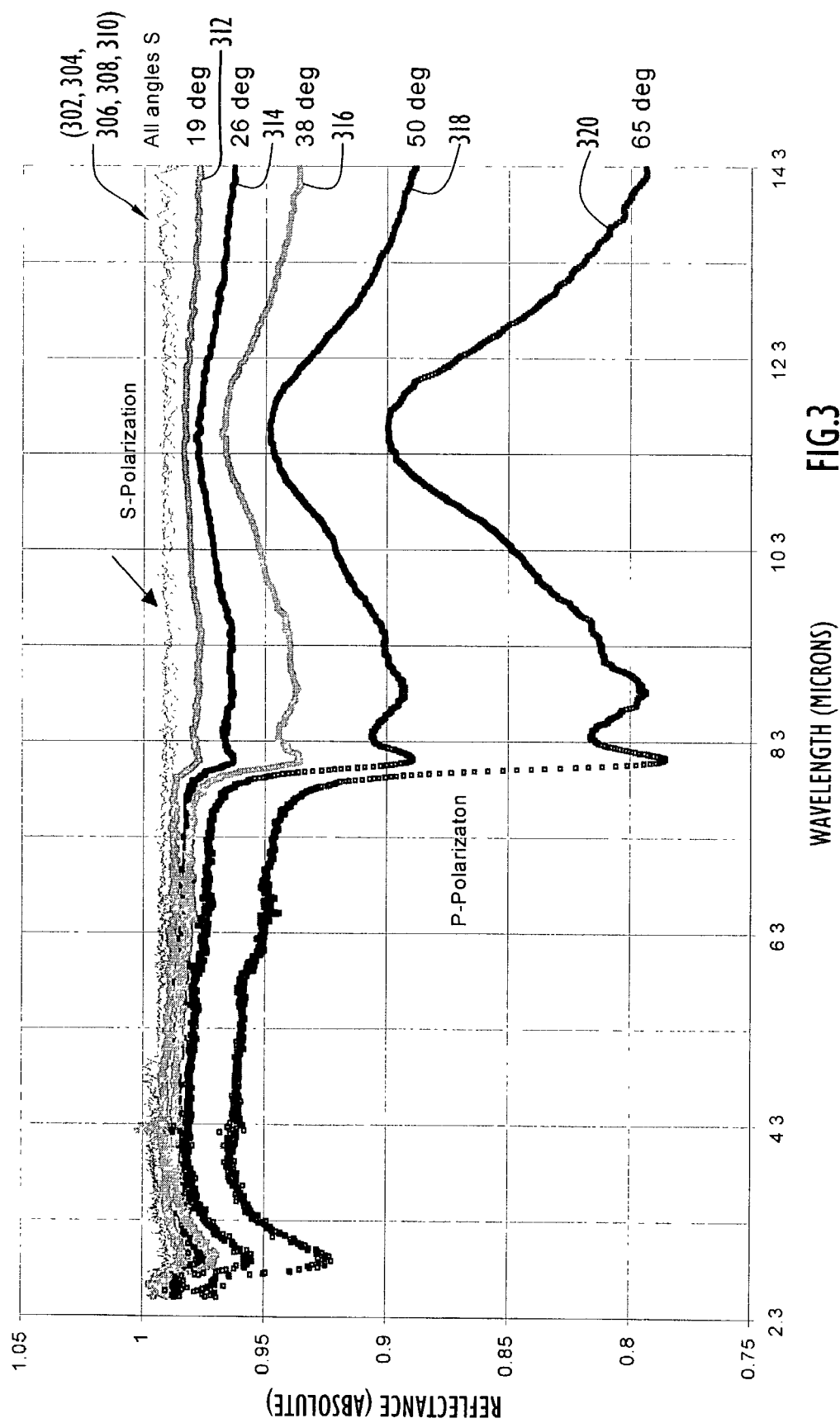
FIG. 3 is a data chart that presents measured S-polarization reflectance values and P-polarization reflectance values versus wavelength for five angles of incidence (i.e., 19°, 26°, 38°, 50° and 65°) for a mirror sample representative of that used by a Moderate Resolution Imaging Spectroradiometer (MODIS).

FIG. 3 is a data chart that presents measured S-polarization reflectance and P-polarization reflectance versus wavelength for five angles of incidence (i.e., 19°, 26°, 38°, 50° and 65°) for a mirror representative of that used by a MODIS instrument on the TERRA satellite, as introduced above. As in the case for the GOES mirror reflectance values shown above, the MODIS scan mirror S-polarization reflectance values show very little dependence on angle of incidence. In fact, as shown in FIG. 3, all S-polarization curves for an angle of incidence of 19° (302), 26° (304), 38° (306), 50° (308), and 65° (310), are near 100% at all wavelengths, as would be expected from the Fresnel equations as discussed in relation to FIG. 1. As further shown in FIG. 3, P-polarization curves for an angle of incidence of 19° (312), 26° (314), 38° (316), 50° (318), and 65° (320), vary significantly more as a function of wavelength.

Although no data is shown in FIG. 3 for reflectance at normal incidence (i.e., 90°), it should be pointed out, again as supported by and described in relation to FIG. 1, that, for highly reflective surfaces (i.e., surfaces for which $n^2+k^2>>1$), S-polarization reflectance values are very nearly 1, and almost equivalent to the near-normal reflectance values of the P-polarization. This results because at near-normal incidence the electric field vectors of the S-polarization and P-polarization are equivalent.

Figure 4:
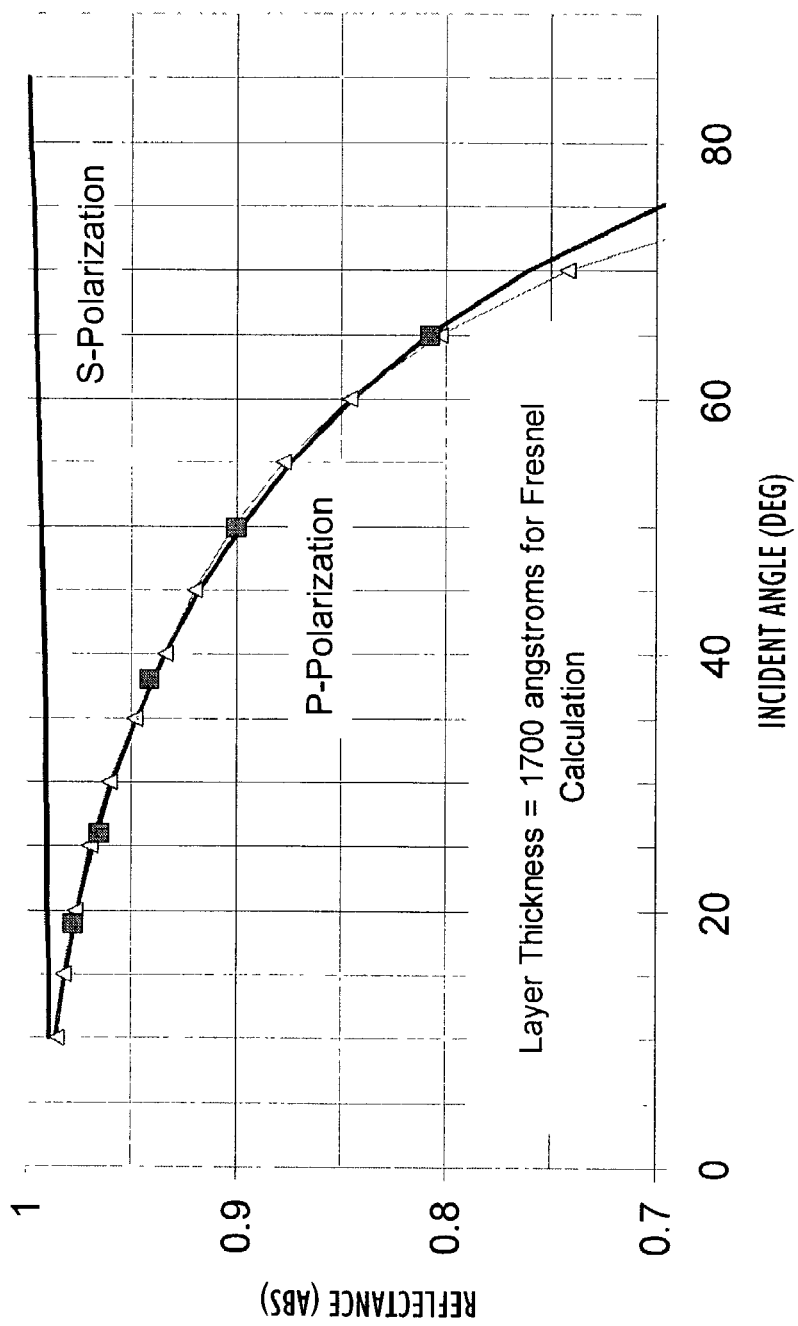
FIG. 4 is a data chart that compares scaled reflectance values calculated in accordance with the teachings of the present invention with measured MODIS reflectance values and reflectance values calculated using traditional Fresnel reflectance equations. Scaled alpha values, calculated in accordance with the teachings of the present invention, for angles of incidence less than 38° have been scaled by 0.93 and alpha values calculated for angles of incidence greater than 38° have been scaled by 0.71.

FIG. 4 presents representative MODIS S-polarization reflectance values 402 and P-polarization reflectance values 404 versus angle of incidence for a single wavelength. In FIG. 4, measured MODIS data points at 406 are plotted along-side P-polarization reflectance values 408 calculated using the angle of incidence-based exponential equations (i.e., Equation (3) and Equation (7)). The reflectance values calculated using the angle of incidence-based Fresnel approximation equations are scaled in the same manner as the reflectance values presented in FIG. 10 (i.e., using a scale factor of 0.93 for θ<38°; and using a scale factor of 0.71 for θ>38°).

As demonstrated in FIG. 4, there is a high level of correlation between the measured data points and calculate reflectance using the angle of incidence-based Fresnel approach, described herein. The angle of incidence-based Fresnel approximation equations can be used to generate accurate reflectance values for multiple angles of incidence, based upon measured reflectance values at a single angle of incidence. This approach, based upon known and accepted Fresnel equations, along with the use of approximated value substitutions (e.g., use of a measured S-polarization reflectance value as a substitute for the P-polarization reflectance at normal, $R_0$) can thus be used to improve confidence in reflectance data for mirror and remote-sensing instrument calibration purposes. One can also quickly assess the quality of reflectance data as it is being acquired, thereby providing opportunity for substantially reducing uncertainties associated with the measurement process, as well as reducing the number of required reflectance measurements as a function of incident angle.

As previously described, algorithms for calculating the effect of angle of incidence on instrument throughput are typically developed by fitting such measured reflectance values with a second (or possibly higher) order polynomial equation. The second order polynomial equation is then used as the basis for estimating the effect of angle of incidence on instrument throughput at other angles of incidences. As previously discussed, while such polynomials fit the data to a rather high degree of accuracy, a polynomial is not a true representation of the expected behavior of the mirror as a function of incidence angle. In particular, built-in measurement errors are unaccounted for in the polynomial fitting process.

By applying the angle of incidence-based exponential equations (i.e., equations 3, 6, and 7), described above, a better representation of an instrument's response as a function of angle of incidence can be calculated using a physically-based model. This angle of incidence, Fresnel-based equation provides more confidence in the analysis of the data than can be achieved using a polynomial fit approach. The angle of incidence-based exponential equations, therefore, are capable of being used to validate subsets of measured data and to identify, and correct for, errors identified in the measured data. More importantly, assuming that $\alpha$ is constant over ranges of angle of incidence, the angle of incidence-based exponential equation can be used to generate estimated reflectance values for multiple angles of incidence, based upon measured reflectance values at a single angle of incidence.

As previously discussed, P-polarization reflectance values and S-polarization reflectance values are high (ideally approaching a value of 1) and very nearly the same at normal incidence ($n^2+k^2>>1$), and S-polarization reflectance changes little with angle of incidence. Using Equation (7), a set of experimentally derived values for $\alpha(\lambda)$ can be calculated using the measured S-polarization reflectance value at $\lambda$, and at small incidence angles (normal incidence is not usually available because of measurement difficulties) as a substitute for the P-polarization reflectance at normal incidence (i.e., for $R_0(\lambda)$). Measured P-polarization reflectance values, at the same specific wavelength, $\lambda$, and at other angles of incidence, are used in Equation 7 for $R_p(\lambda)$. Assuming $\alpha(\lambda)$ remains constant over a range of incidence angles, experimentally derived values for $\alpha(\lambda)$ are used in Equation (3) to estimate P-polarization reflectance values for the specific wavelength of light as a function of angle of incidence (i.e., θ), wherein θ is a different angle of incidence for which $\alpha(\lambda)$ was determined using the above method. It should be noted that, as described in Equation (5), $\alpha$ is a function of $\lambda$, and depends on the indices of refraction (n) and absorption coefficients (k) for the various layers, which are not known, especially for a multilayer structure of thin films such as a coated mirror surface. By calculating $\alpha$ using Equation (7) and data measured at a specific wavelength and angle of incidence, a useful value of $\alpha$ at the specific wavelength is ascertained without detailed knowledge of n and k.

Figure 5:
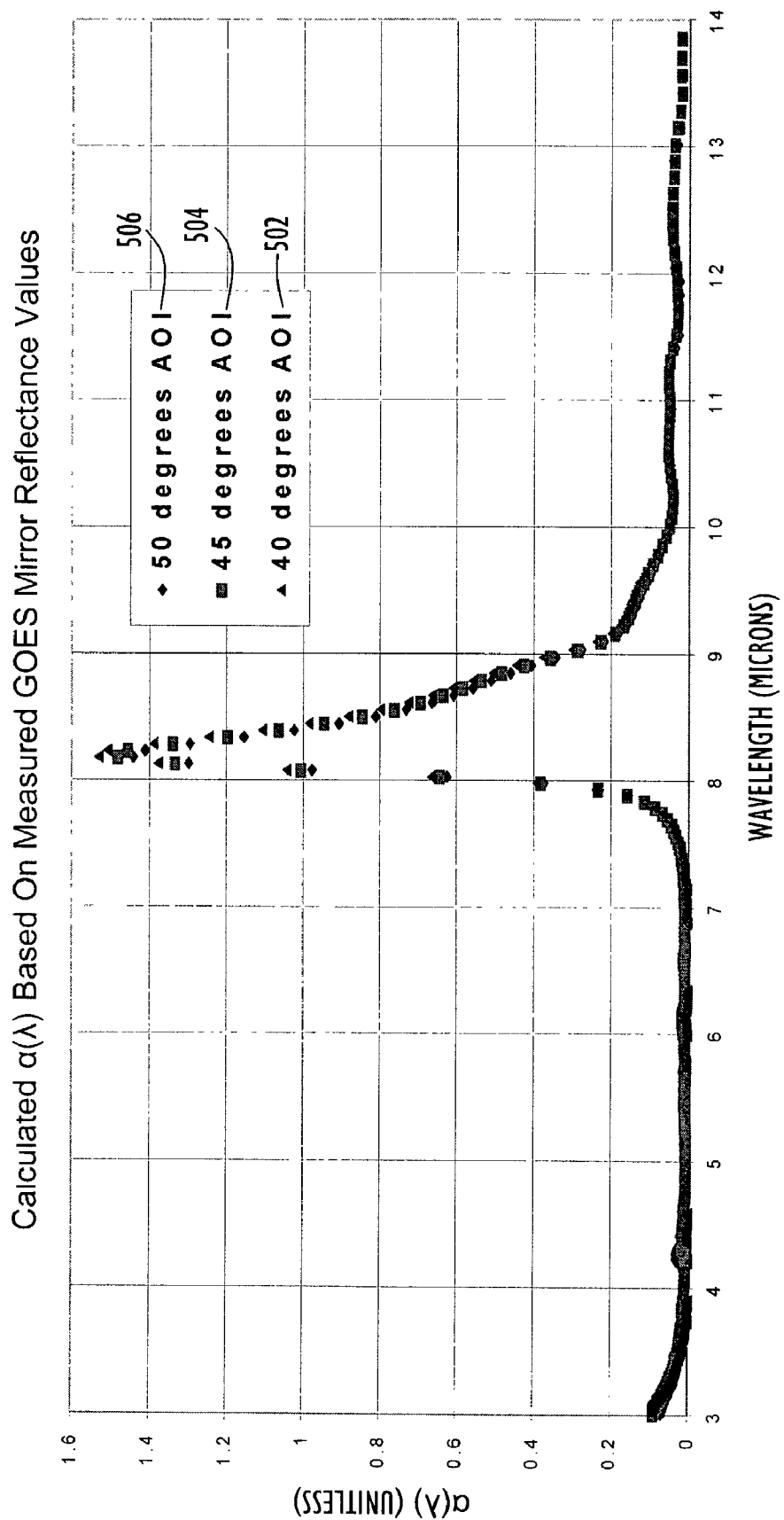
FIG. 5 is a data chart that presents representative values of alpha (i.e., $\alpha(\lambda)$) versus wavelength, calculated, in accordance with an exemplary embodiment of the invention, using the measured GOES mirror sample P-polarization reflectance values presented in FIG. 2 for the three respective angles of incidence (40°, 45°, and 50°).

FIG. 5 shows values of alpha (i.e., $\alpha(\lambda)$) versus wavelength, calculated using the measured GOES mirror sample P-polarization reflectance values presented in FIG. 2 for the three respective angles of incidence (40°, 45°, and 50°). In FIG. 5, calculated values of alpha (i.e., $\alpha(\lambda)$) for an angle of incidence of 40° are shown at 502, for an angle of incidence of 45° at 504, and for an angle of incidence of 50° at 506. Note that the $\alpha$ values are very nearly identical with only a slight difference between the values for each of the three angles. This is as expected, based on Equation (7), where the only dependence of $\alpha$ is on wavelength in our model. As will be described in greater detail in relation to the measured MODIS mirror data (see FIG. 3), $\alpha$ is nearly constant for finite ranges of angle of incidence and can be used to estimate reflectance at other angles of incidence using a small number of range-specific scaling factors for $\alpha$. The range of angles over which $\alpha$ is approximately constant is determined is based upon an analytical comparison of the calculated values to measured data.

Figure 6:
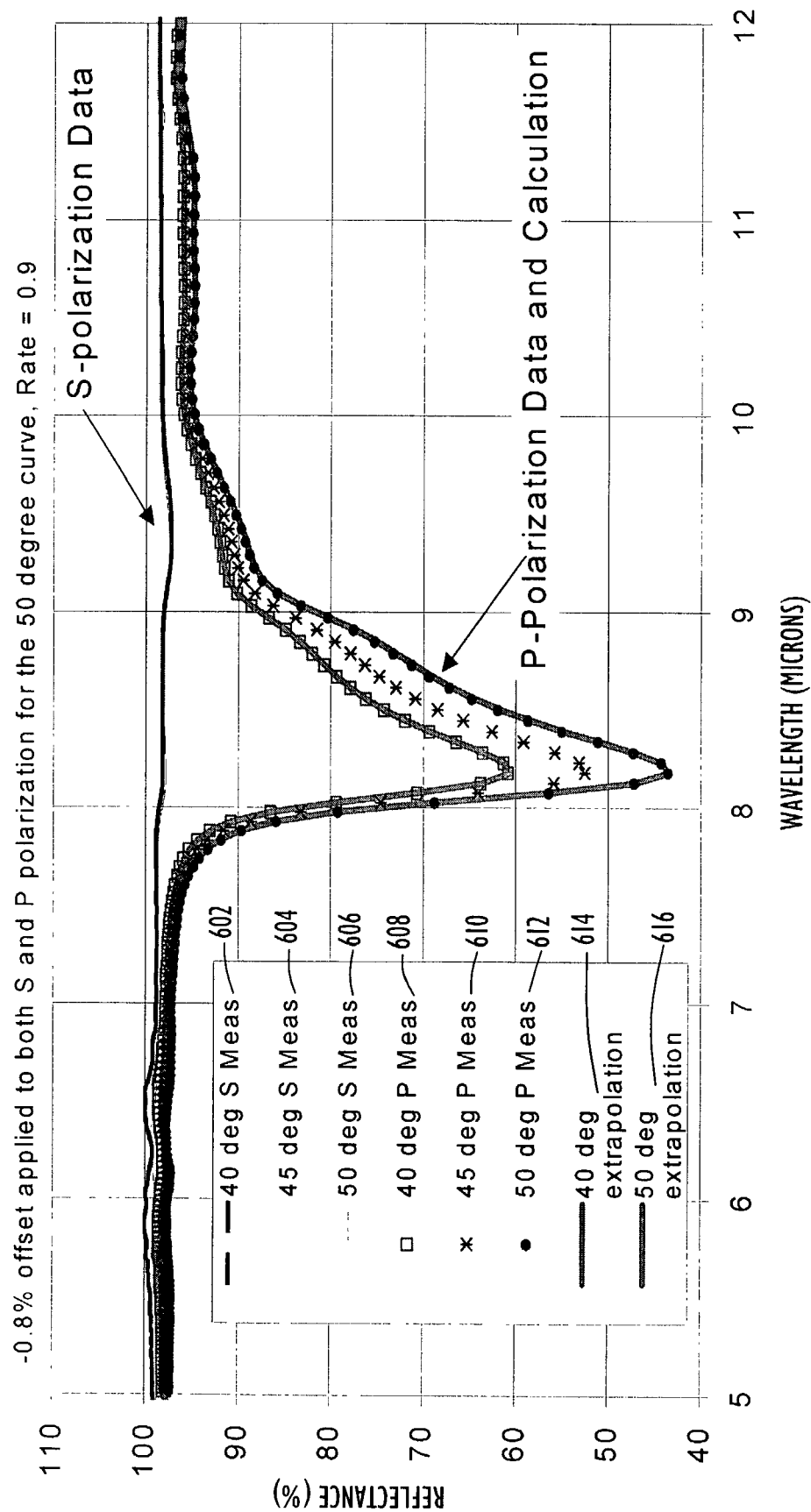
FIG. 6 is a data chart that presents representative S-polarization reflectance values and P-polarization reflectance values versus wavelength, in which the values measured for reflectance at 45° are used as the basis for calculating reflectance values for P-polarization at 40° and 50°, after a −0.8% offset is applied to correct the reflectance values for P-polarization at 50°, in accordance with an exemplary embodiment of the invention.

For example, the GOES data given in FIG. 6 shows that for small ranges of angles (~10–15 degrees) about a specific angle (in this case 45°) $\alpha$ can be held constant (with a scaling factor) and provide a good fit to the measured data. Confidence in the data as a function of angle is thus increased because the present physically-based analysis process and the measured data agree in functional form with incidence angle. For the MODIS data, $\alpha$ cannot be held constant over the entire range of angles (19–65 degrees) for which data exists. To achieve the fit to this measured data two separate scaling factors for $\alpha$ in the angular range of 19–38 degrees and 38–65 degrees are used. Assessment of the need for $\alpha$ scaling factors is also based upon an analytical comparison of calculated values to measured data. Based on the present analysis it appears that, in general, one or two scaling factors are required for most mirror types.

This technique employs a method for assessing the quality of reflectance data by taking advantage of a phenomenological fitting equation for the data. If a mirror surface becomes contaminated in application or in practice, alpha will likely change, making it necessary to recalculate values for alpha, reassess the range over which alpha can be approximated as constant, and recalculate required scaling factors, using the techniques described.

FIG. 6 demonstrates that reflectance values measured across a spectrum of wavelengths at a specific angle of incidence can be used to calculate reflectance values at other specific angles of incidence across the same spectrum of wavelength, in accordance with the teachings of the present invention. Specifically, in FIG. 6, the S-polarization reflectance values and P-polarization reflectance values versus wavelength curve for a GOES mirror, for light at a 45° angle of incidence (shown in FIG. 6 at 610), is used as a reference to calculate the reflectance curves for angles of incidence of 40° (shown in FIG. 6 at 614) and 50° (shown in FIG. 6 at 616), respectively, using Equation (3) and a scaled average α calculated from the data in FIG. 5.

In FIG. 6, P-polarization reflectance values for 40° (at 614) and 50° (at 616) angles of incidence, were calculated by substituting a measured S-polarization reflectance value (shown in FIG. 6 at 604) at each specific wavelength for normal incidence P-polarization reflectance (i.e., for $R_0(\lambda)$ in Eqn. 3), and substituting for $\alpha(\lambda)$ a scaled average of the α values, shown in FIG. 5, calculated for the same corresponding wavelength. Agreement between the measured reflectance and the extrapolated reflectance using the present invention is excellent, illustrating the utility of the present invention. (Note that measured values for S-polarization reflectance at 40° and 50° angles of incidence are also depicted in FIG. 6 at 602 and 606, respectively. The plots of these values overlap with the values associated with S-polarization reflectance values at a 45° angle of incidence, and are essentially identical after a measurement artifact is removed. Both S-polarization and P-polarization measurements at 50° apparently suffered from a 0.8% offset relative to the 40° and 45° measurements. (As noted on FIG. 6 both S and P-polarization 50° reflectance curves were offset by −0.8% to bring the 40°, 45°, and 50° S-polarization reflectances into agreement as they should closely agree both practically and theoretically according to the Fresnel equations. This step was taken since both the P and S measurements at 50° exhibited the same apparent offset. The offset cannot be explained physically, and is therefore assumed to be an inaccuracy, or artifact, associated with the measurement process. In this manner, the present techniques are used to identify errors, or artifacts, in the measured data.

Figure 7:
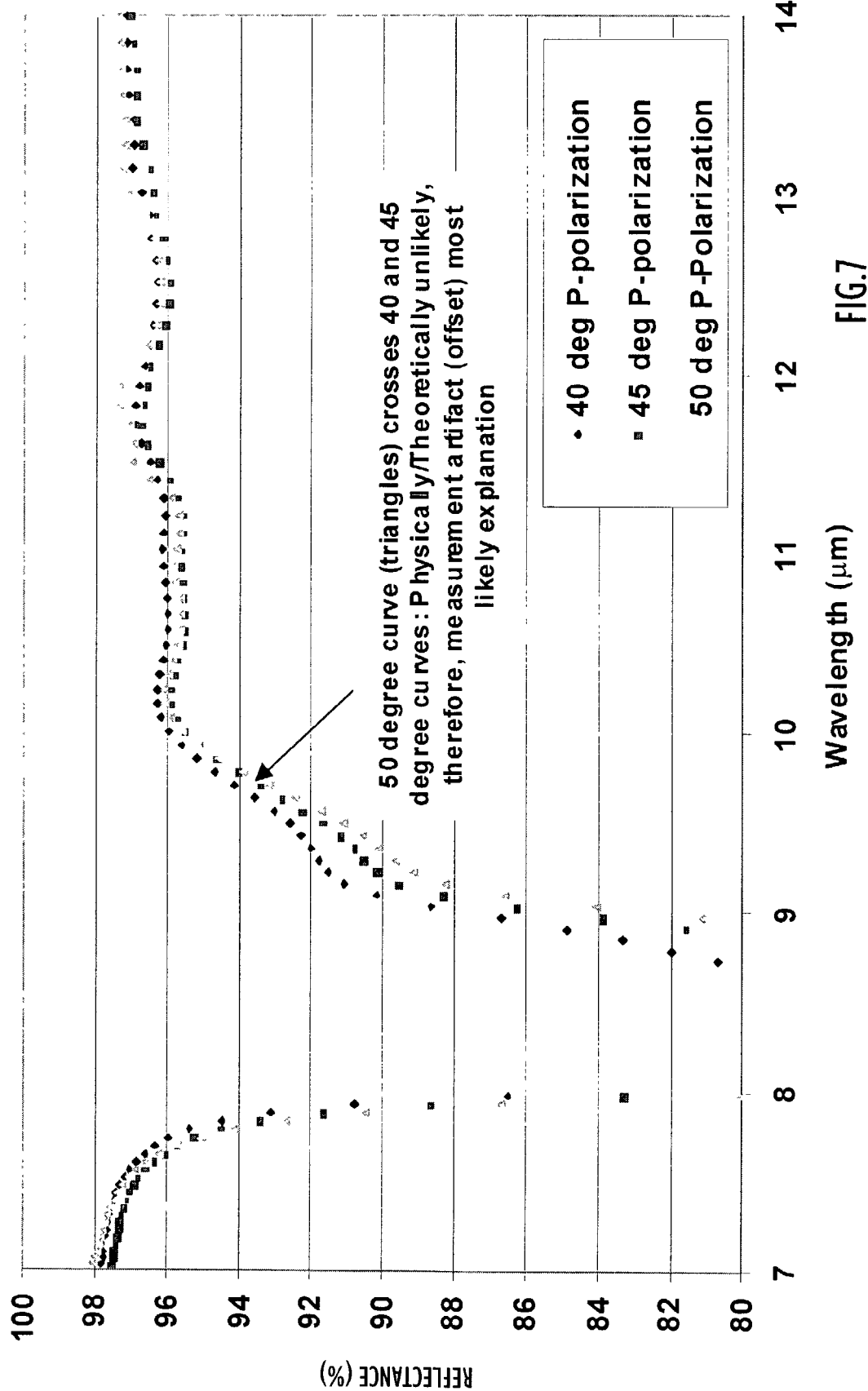
FIG. 7 is a data chart presenting a detailed view of the same S-polarization reflectance values and P-polarization reflectance data versus wavelength presented in FIG. 2 that more clearly shows an apparent 0.8% offset in the S-polarization reflectance values and P-polarization reflectance values measured at a 50° incident angle.

FIG. 7 is a data chart presenting an expanded view of the raw P-polarization reflectance data versus wavelength presented in FIG. 2. As shown in FIG. 7 the 50° curve crosses over the 40° and 45° curves near 9.7 microns, or at about 96% reflectance. The P-Polarization data for 50° appears offset from the other reflectance curves by approximately +0.8%. Applying a −0.8% offset to both the S-polarization and the P-polarization curves results in the good agreement between the measured and the calculated data shown in FIG. 6 which follows the expected continuous smooth decrease in reflectance as the angle increases. This behavior should be expected based on both Fresnel analysis and the present invention.

The need for scaling factors for α accounts for the fact that the exponential dependence of the angle of incidence function defined here is not exact. Referring to FIG. 1 it can be seen that at higher angles the rate at which the reflectance decreases also decreases with angle. Therefore, scaling of α makes sense, and is physically based.

Based upon FIG. 1, a decrease in reflectivity with an increase in the angle of incidence is to be expected. Given that the angle of incidence-based exponential equations, here described, are a physical model in the same manner as the original Fresnel reflection equations, the angle of incidence-based exponential equations allow a serious and valid consideration of possible errors made during the measurement process and allow identified errors in either the accuracy of the approximated Fresnel equations and/or the measured data to be easily accommodated. Such analysis and corrections cannot be performed using an approach that uses a model derived from the measured data using polynomial curve fitting, as previously discussed, for a fitted polynomial curve is not based upon a physical model of the reflectance phenomenon.

Figure 8:
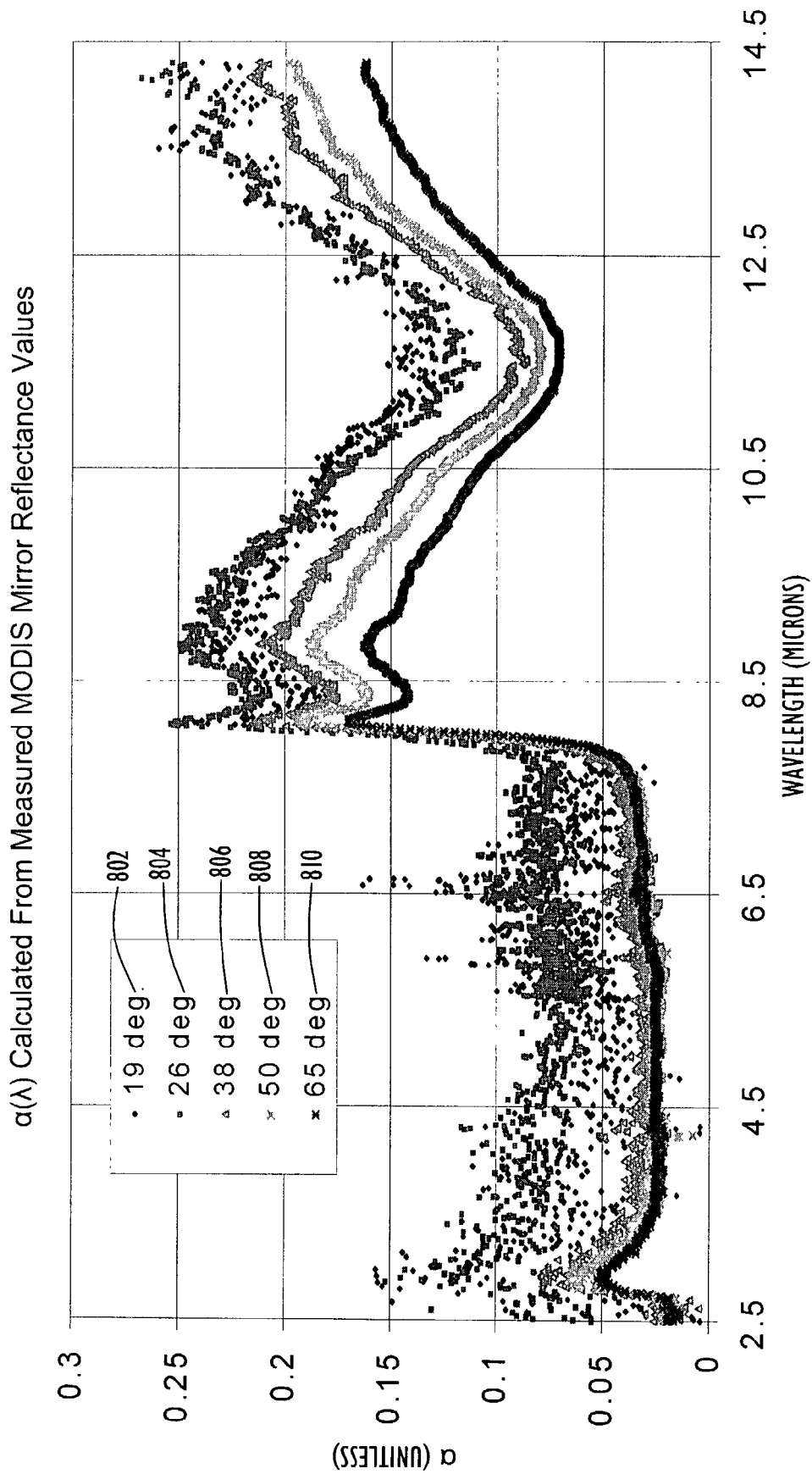
FIG. 8 is a data chart that presents representative values of alpha (i.e., $\alpha(\lambda)$) versus wavelength, calculated using the measured MODIS mirror sample P-polarization reflectance values presented in FIG. 3 for five respective angles of incidence (i.e., 19°, 26°, 38°, 50° and 65°), in accordance with an exemplary embodiment of the invention.

FIG. 8 presents values of alpha (i.e., $\alpha(\lambda)$) versus wavelength, calculated using Equation (7), using the average S-polarization MODIS mirror reflectance data shown in FIG. 3 as reference, $R_0(\lambda)$, and the measured MODIS mirror sample P-polarization reflectance data presented in FIG. 3 for the five respective angles of incidence (19°, 26°, 38°, 50° and 65°), identified in FIG. 8 at 802, 804, 806, 808 and 810, respectively. The MODIS data spans 46° of angle of incidence range (as opposed to the GOES data that only spanned 10°). Therefore, the MODIS data is a good test of how far the present scan-angle approximated Fresnel technique can be taken. Note that the range of values for α are considerably greater for each wavelength than they were for the GOES mirror data, clearly demonstrating that α can vary with angle of incidence.

Figure 9:
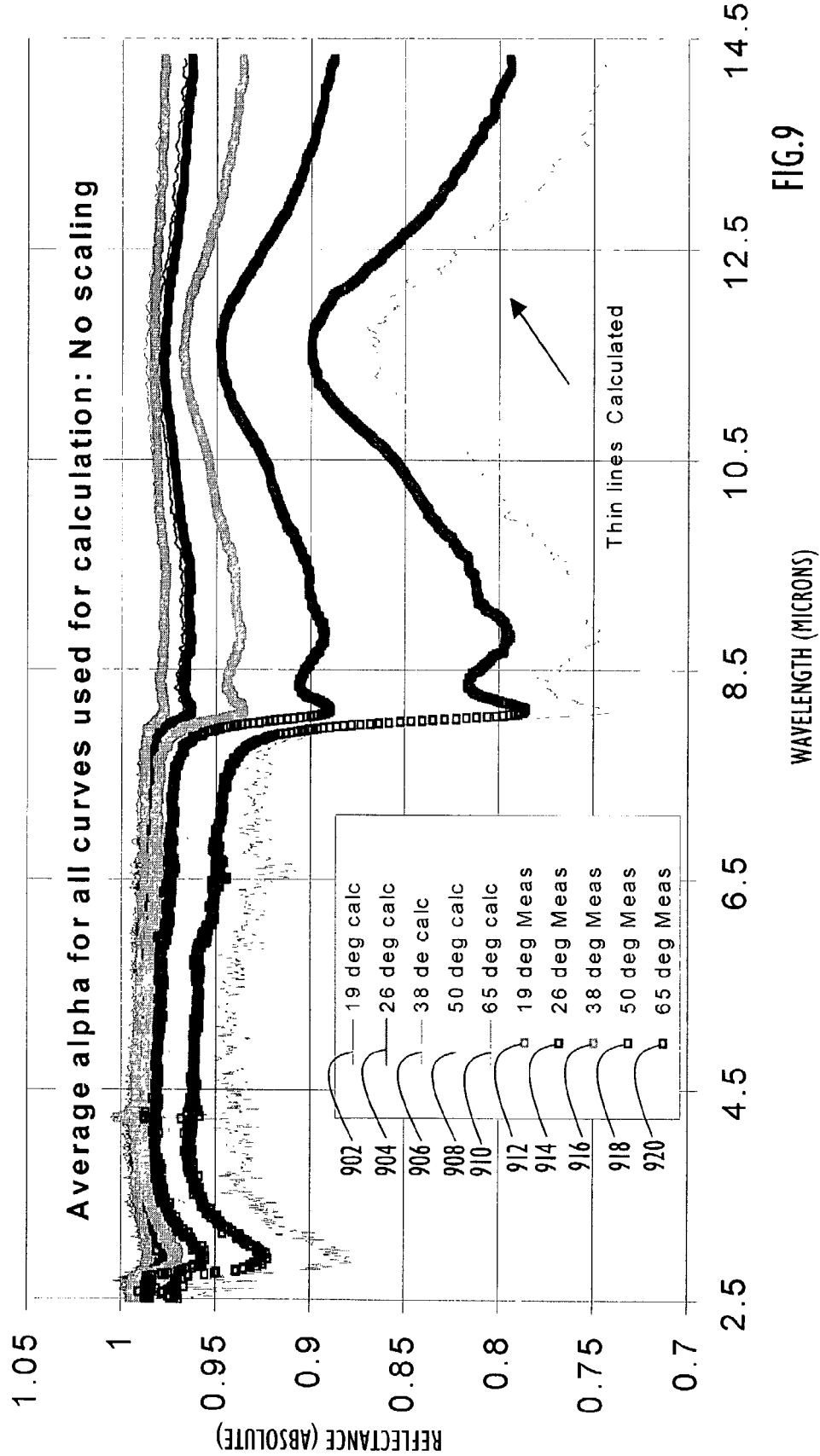
FIG. 9 is a data chart that presents P-polarization reflectance values (calculated at angles of incidence of 19°, 26°, 38°, 50° and 65°) versus wavelength, in accordance with an exemplary embodiment of the invention. The calculated reflectance values were calculated using the measured P-polarization reflectance values at a 38° angle of incidence as reference (from FIG. 3), and an average $\alpha$ calculated, from the values of $\alpha$ presented in FIG. 7.

FIG. 9 presents P-polarization reflectance values versus wavelength (for MODIS data first presented in FIG. 3) in which reflectance values, calculated using angle of incidence-based techniques for angles of incidence of 19°, 26°, 38°, 50° and 65°, identified in FIG. 9 at 902, 904, 906, 908 and 910, respectively, are presented alongside the measured reflectance values for angles of incidence of 19°, 26°, 38°, 50° and 65°, identified in FIG. 9 at 912, 914, 916, 918 and 920, respectively.

The calculated reflectance values are calculated using the measured P-polarization reflectance values at 38° of incidence as a reference, and an average $\alpha(\lambda)$ calculated for each wavelength ($\lambda$) from the values for $\alpha(\lambda)$ determined for each wavelength for each of the five angles of incidence (i.e., 19°, 26°, 38°, 50° and 65°) as shown in FIG. 8. However, no scaling factor has yet been used, as is applied to the reflectance values shown in FIG. 6. As shown in FIG. 9, if the 38° angle of incidence curve is used to calculate values of reflectance at other angles of incidence, reflectance values calculated for angles of incidence above and below 38° are not precisely aligned with the measured data for the same respective angles of incidence.

Figure 10:
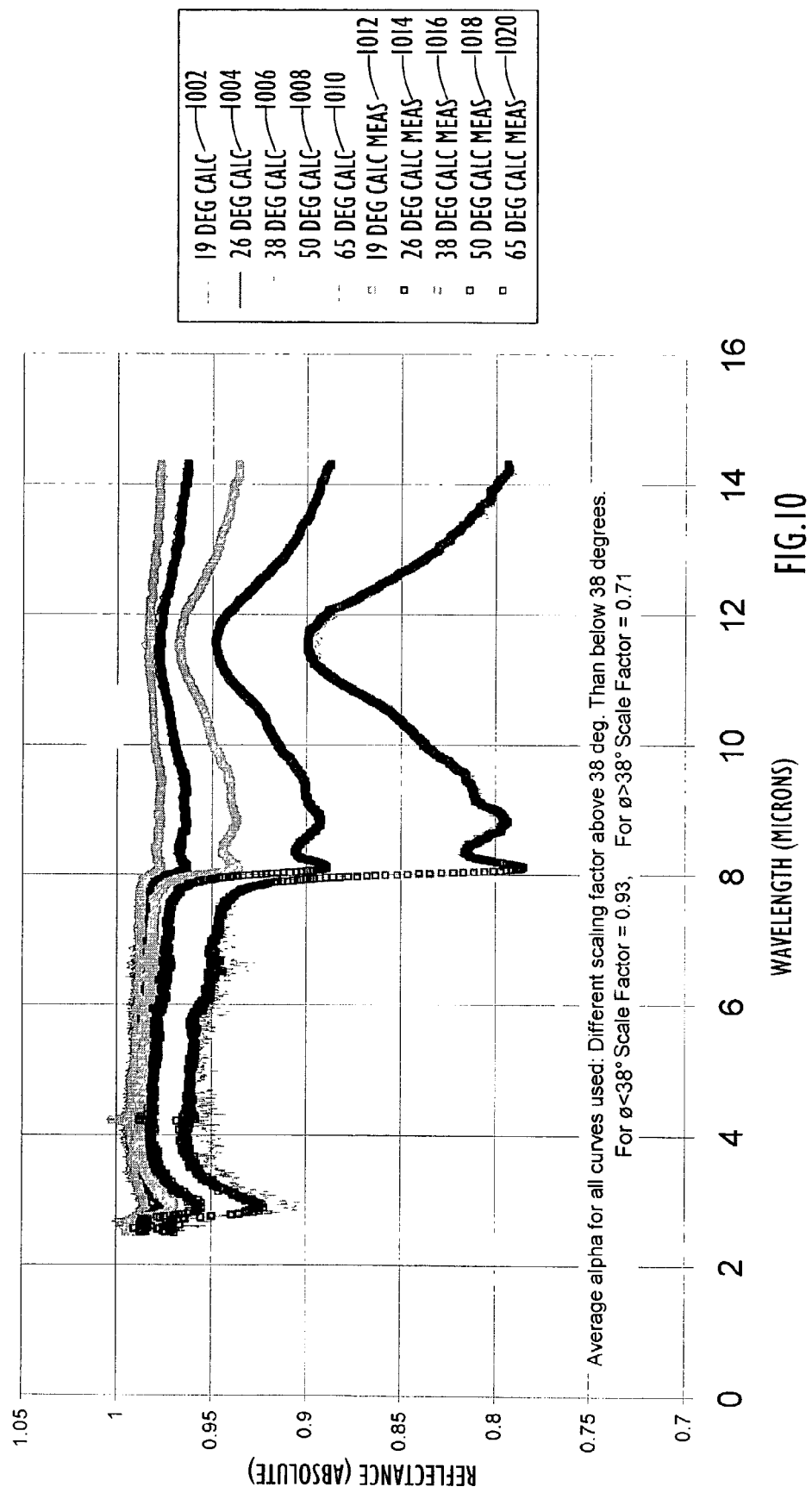
FIG. 10 is a data chart that presents the same MODIS P-polarization reflectance values presented in FIG. 9, in which the alpha values for angles of incidence less than 38° have been scaled by 0.93 and alpha values calculated for angles of incidence greater than 38° have been scaled by 0.71.

FIG. 10 presents the same measured MODIS P-polarization reflectance versus wavelength data as presented in FIG. 9, along with calculated reflectance referenced to the 38° reflectance. For the calculated results the α values (shown in FIG. 8) for angles of incidence less than 38° have been scaled by 0.93, and α values calculated for angles of incidence greater than 38° have been scaled by 0.71. As shown in FIG. 10, once the scaling factors are applied to α, as previously described, the calculated reflectance data for the five respective angles of incidence (i.e., 19°, 26°, 38°, 50° and 65°), identified in FIG. 10 at 1002, 1004, 1006, 1008 and 1010, respectively, closely align with the measured reflectance values for angles of incidence at 19°, 26°, 38°, 50° and 65°, identified in FIG. 10 at 1012, 1014, 1016, 1018 and 1020, respectively.

Figure 11:
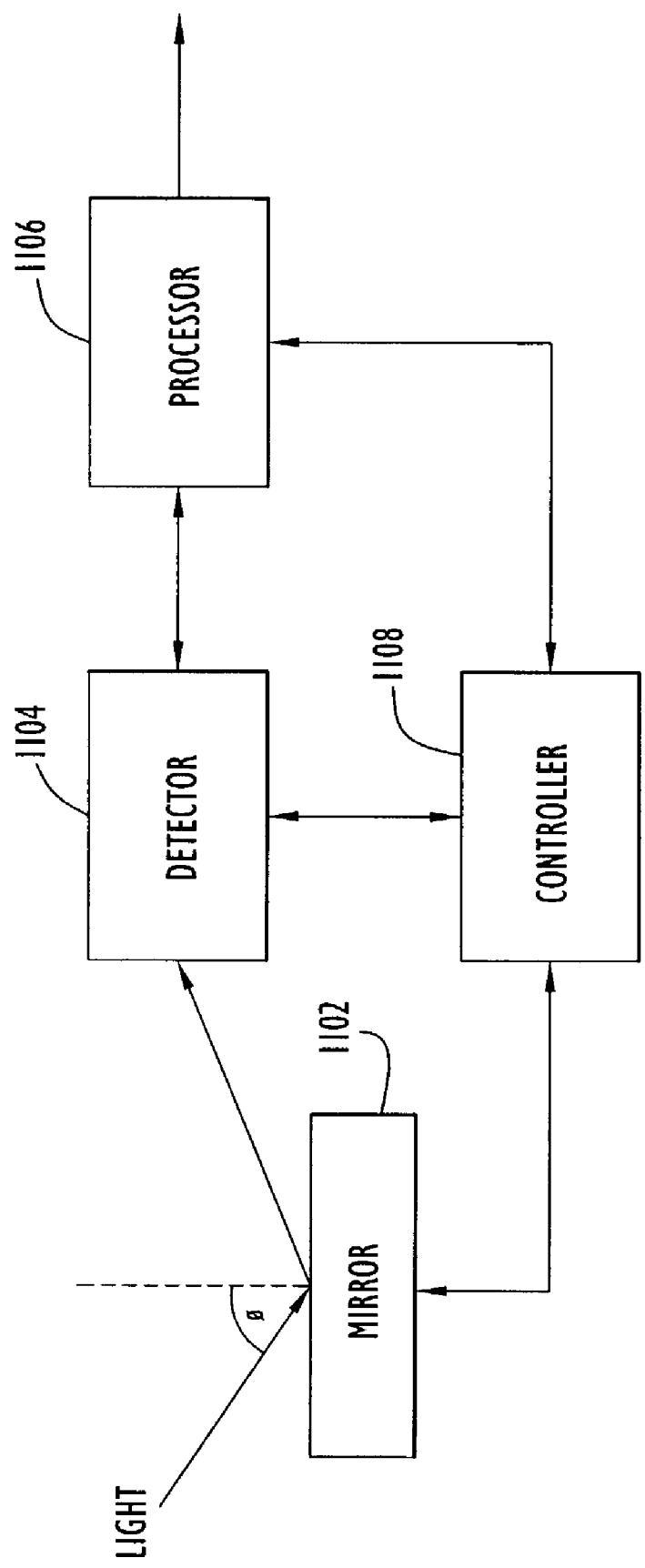
FIG. 11 is a block diagram depicting representative modules within a representative apparatus capable of assessing mirror reflectance using an angle of incidence-based approach in accordance with an exemplary embodiment of the invention.

FIG. 11 presents a block diagram depicting representative modules within a representative apparatus capable of assessing mirror reflectance using an angle of incidence-based approach in accordance with an exemplary embodiment of the invention. As depicted in FIG. 11, light impacts and is reflected by a scanned mirror 1102 and detected by a detector 1104 that quantifies the amount of light received at one or more wavelengths.

The detector 1104 transmits the quantified value to a processor 1106 for processing in accordance with the teachings of the present invention. In one exemplary, non-limiting embodiment, the detector determines the angle of incidence based upon information received from the scan mirror 1102 and/or the controller 1108. The detector 1104 then transmits to the processor 1106 the angle of incidence and/or the wavelength of the light, along with the quantized measurement.

In another exemplary, non-limiting embodiment, the processor 1106 controls the angle of incidence and/or wavelength of light measured by the detector 1104 via commands to the controller and/or detector. Angle of incidence and/or wavelength information, therefore, does not need to be received with the measured reflectance values. In yet another exemplary, non-limiting embodiment angle of incidence, wavelength and/or reflectance values are stored by the processor and used in subsequent processing.

The processor gathers information associated with mirror calibration and/or operational data collection by issuing instructions to a controller 1108 for the collection of light at one or more wavelengths and at one or more angles of incidence. In response to such instructions from the processor, the controller 1108 configures the detector and/or the scanned mirror 1102 to collect information in accordance with instructions received from the processor. Scan mirror calibration and/or correction of collected data based upon calibration techniques described herein can be executed in parallel with data collection or executed upon previously stored data values. Alternatively, quantized measurements, angle of incidence measurements, and associated wavelength information received from the processor can be transmitted to a remote device for processing.

Figure 12:
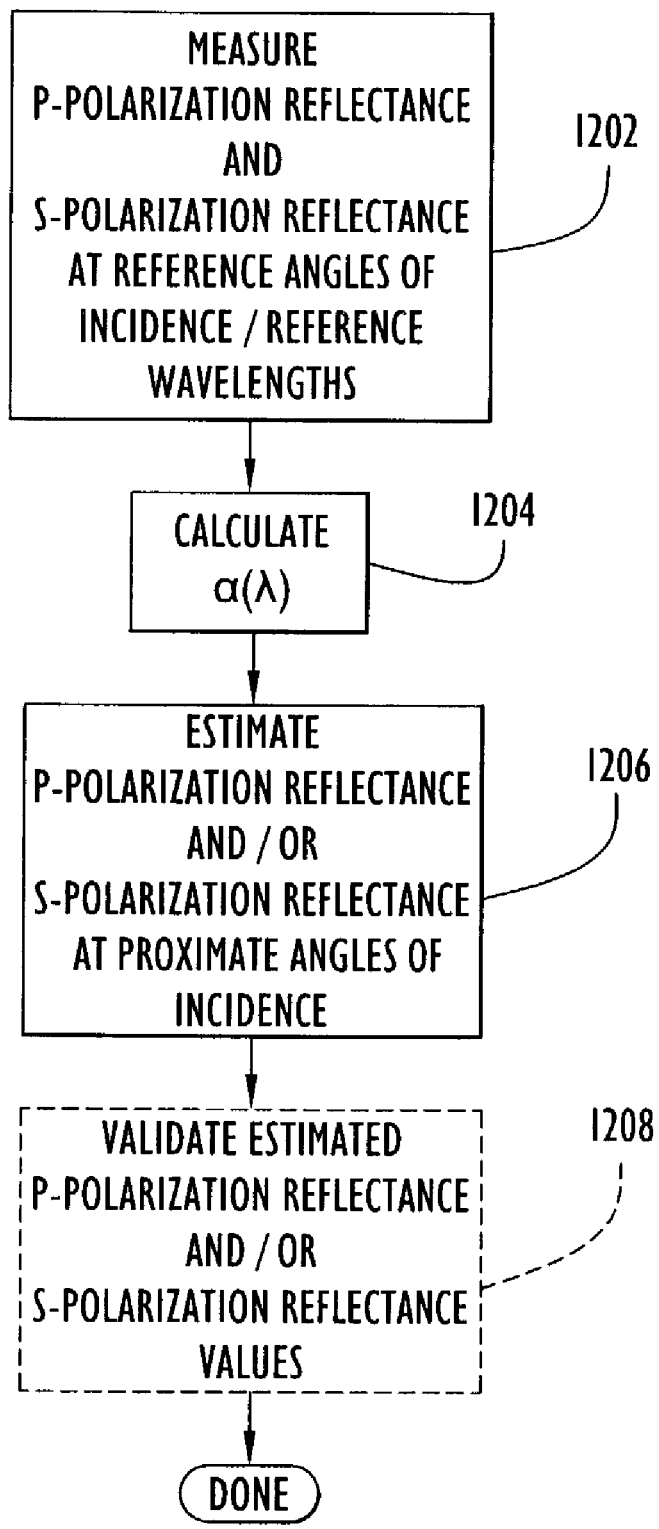
FIG. 12 is a flow diagram presenting a representative functional flow capable of assessing mirror reflectance using an angle of incidence-based approach in accordance with an exemplary embodiment of the present invention.

FIG. 12 presents a representative operational flow capable of being executed by an apparatus, such as the apparatus described in relation to FIG. 11, operating in the field or within a laboratory or similar environment, for assessing/calibrating mirror reflectance, and/or for correcting collected data, using an angle of incidence-based approach in accordance with an exemplary embodiment of the present invention. First, a scan mirror is selected for assessment, and one or more reference angles of incidence ("angle of incidence" is abbreviated as "AOI" in FIG. 12) and reference wavelengths are selected for assessing the scan mirror characteristics. The criteria used for angle of incidence and wavelength selection can vary. For example, if a scan mirror uses materials for which n and k are known to vary significantly in a specific region of the spectrum, additional measurements can be taken at wavelengths in proximity to and/or within that region of the spectrum. In addition, if $\alpha$ for a specific type of mirror, is known to vary significantly over a specific range of angles of incidence, additional measurements can be taken within proximity to that range of angles of incidence.

Once the reference angles of incidence and reference wavelengths have been selected, S-polarization and P-polarization reflectance values are collected and stored 1202 for the selected reference wavelengths at the selected reference angles of incidence. Next, a value of $\alpha$ is calculated, using Equation (7), for each reference wavelength/reference angle of incidence pair 1204.

As discussed in relation to FIGS. 5 and 8, calculated values for $\alpha$ can be relatively constant for a single wavelength, over a range of angles of incidence. However, depending upon scan mirror characteristics, $\alpha$ can also vary as a function of angle of incidence. To quantify the rate of variation in $\alpha$ as a function of angle of incidence, and hence the range of angle of incidence, within proximity of a reference angle of incidence over which $\alpha$ can be approximated as constant, the calculated $\alpha$ values are assessed, using a number known statistical techniques. In one non-limiting embodiment, and average $\alpha$ is calculated for a set of reference angles of incidence for a reference wavelength. In another non-limiting embodiment, the statistical distribution of $\alpha$ over the range of reference angles of incidence is determined and used to estimate a likely value for $\alpha$ for a specific angle of incidence. In yet another non-limiting embodiment, a linear or polynomial equation is calculated by which $\alpha$ can be calculated as a function of angle of incidence for a single wavelength. In one non-limiting representative embodiment, the $\alpha$ assessment process is used to select a set of angles of incidence proximate to each reference angle of incidence for which $\alpha$ can be assessed to a high degree of accuracy. These proximate angles of incidence are used to calculate reflectance values using the angle of incidence-based reflectance calculations (e.g., Eqs. 3 and 6). Proximate angles of incidence are also selected to provide sufficient coverage over of the angle of incidence/wavelength spectrum of interest.

Once all reference measurements have been made, their associated information stored, the calculated values of $\alpha$ assessed, and proximate angles of incidence selected, angle of incidence-based reflection values are estimated for each reference wavelength for each designated proximate angle of incidence, in accordance with the teachings of the present invention.

First, a proximate angle of incidence is selected from those identified, as described above. As previously described, proximate angles of incidence are sufficiently close to a reference angle of incidence that the value of $\alpha$ calculated for the reference angle of incidence can be assumed to be constant (i.e., can be used as a sufficiently accurate approximation to $\alpha$ at the proximate angle of incidence to support calculation of reflectance values for the proximate angle of incidence). Alternatively, depending upon the characteristics of $\alpha$ determined, an accurate value of $\alpha$ for the proximate angle of incidence can be calculated, as described above.

Next, at operation 1206, S-polarization and P-polarization reflectance values are estimated for the proximate angle of incidence across the spectrum of reference wavelengths using Equation (3) and Equation (6), as previously described. In highly reflective surfaces (i.e., in which $n^2+k^2>>1$) the S-polarization reflectance is nearly the same as the P-polarization reflectance at normal incidence, as previously described. Therefore, in calculating reflectance values for a proximate angle of incidence using Equation (3), the S-polarization reflectance value at normal incidence is substituted for the P-polarization at normal incidence (i.e., $R_0(\lambda)$), and values of $\alpha(\lambda)$ (calculated for the same wavelength at the reference angle of incidence), are substituted for $\alpha(\lambda)$. In this manner, accurate estimates of reflectance are generated for each specific wavelength of the spectrum of reference wavelengths using Equation (3) as a function of angle of incidence (i.e., $\theta$) without a need for knowledge of n and k, as previously described.

Optionally, a small set of S-polarization and P-polarization data points is measured for the proximate angle of incidence for use in validating 1208 the reflectance values, calculated using Equation (3) and Equation (6) for the proximate angle of incidence. If the measured and calculated reflectance values do not align within a user-configurable tolerance range, validation results are used to calculate a scalar offset that is applied to the calculated data points to optimize correlation. If reflectance values have been calculated for each designated proximate angle of incidence, processing stops, otherwise, processing continues for another proximate angle of incidence at operation.

By applying the angle of incidence-based exponential equations (i.e., equations 3, 6, and 7), described above, a better representation of an instrument's response as a function of angle of incidence can be calculated using a true physical model. This angle of incidence-based exponential equation approach suffers from less error than can be achieved using a polynomial fit approach. The angle of incidence-based exponential equations, therefore, are capable of being used to validate subsets of measured data and to identify, and correct for, errors identified in the measured data. More importantly, the angle of incidence-based exponential equation can be used to generate accurate reflectance values for multiple angles of incidence, based upon measured reflectance values at a single angle of incidence.

Using Equation (7), a set of experimentally derived values for $\alpha(\lambda)$ can be calculated using the measured S-polarization reflectance value at a specific wavelength and at a specific angle of incidence as a substitute for the P-polarization reflectance at normal (i.e., for $R_0(\lambda)$), and the measured P-polarization reflectance value, at the same specific wavelength and at the same specific angle of incidence, as a substitute for $R_p(\lambda)$. By assuming that $\alpha(\lambda)$ remains constant over a range of angles of incidence, experimentally derived values for $\alpha(\lambda)$ are used in Equation (3) to estimate P-polarization reflectance values for the specific wavelength of light as a function of angle of incidence (i.e., $\theta$), wherein $\theta$ is a different angle of incidence for which $\alpha(\lambda)$ was calculated. By calculating $\alpha$ using the angle of incident based approach (i.e., Equation (7)) and data measured at a specific wavelength and angle of incidence, an accurate value $\alpha$ is ascertained without detailed knowledge of n and k.

Instructions for controlling the mirror, detector, controller and processor to measure S-polarization reflectance, measure P-polarization reflectance and to perform the processing and other operations, as described above, can be implemented as software instruction modules readable and executable within the detector, controller and processor, respectively. It is to be understood that the software can be implemented in virtually any desired computer language and can be developed by one of ordinary skill in the computer arts based on the descriptions contained here and the flow charts illustrated in the drawings. The detector, controller and processor, as described above, can be implemented by hardware or other processing circuitry, including firmware. The various control functions of the mirror, detector, controller, and processor can be distributed in a variety of manners among practically any quantity of computer or processing systems or circuitry and/or among practically any quantity of software and/or hardware units or modules. The software and/or algorithms described above and illustrated in the flow charts can be modified in a manner that accomplishes the functions described herein.

Having described preferred embodiments of methods and apparatus for analyzing mirror reflectance, it is believed that other modifications, variations and changes will be suggested to those skilled in the art in view of the teachings set forth herein. It is, therefore, to be understood that all such variations, modifications and changes are believed to fall within the scope of the present invention as defined by the appended claims. Although specific terms are employed herein, they are used in their ordinary and accustomed manner only, unless expressly defined differently herein, and not for purposes of limitation.

What is claimed is:

1. A method of determining the reflectance of a mirror as a function of angle of incidence, comprising:
   (a) measuring the P-polarization reflectance of the mirror at a reference angle of incidence relative to the normal of a reflective surface of the mirror;
   (b) measuring the S-polarization reflectance of the mirror;
   (c) computing an approximation of at least one of the S-polarization reflectance and the P-polarization reflectance at a proximate angle of incidence other than the reference angle from the measured S-polarization and P-polarization reflectances.

2. The method of claim 1, wherein (h) includes measuring the S-polarization reflectance of the mirror at the reference angle of incidence.

3. The method of claim 1, wherein (c) includes computing an approximation of at least one of the S-polarization reflectance and the P-polarization reflectance over a range of angles of incidence from the measured S-polarization and P-polarization reflectances.

4. The method of claim 1, wherein steps (a), (b) and (c) are repeated at a plurality of wavelengths of incident light.

5. The method of claim 1, further comprising:
   (d) correcting measurements of a signal received via the scanning mirror in accordance with at least one of S-polarization and P-polarization reflectances computed in (c).

6. The method or claim 1, wherein a calculated reflectance value calculated for the reference angle of incidence is compared to at least one measured reflectance value measured at the reference angle of incidence to calculate a scalar value that is applied to reflectance values calculated for the reference angle of incidence for other wavelengths.

7. The method of claim 1, wherein (c) includes treating the measured S-polarization reflectance of the mirror as an approximation of the P-polarization reflectance at normal incidence.

8. The method of claim 7, further comprising computing a value of $\alpha(\lambda)$ determined by $$\alpha(\lambda) = \frac{\ln[R_P(\lambda)/R_0(\lambda)]}{1 - \sec(\theta_R)};$$

wherein $\theta_R$ is the reference angle of incidence, $R_p(\lambda)$ is the P-polarization reflectance measured at the reference angle of incidence $\theta_R$ at a wavelength $\lambda$, and $R_0(\lambda)$ is the P-polarization reflectance at normal incidence approximated by the S-polarization reflectance measured at the reference angle of incidence $\theta_R$.

9. The method of claim 8,
   wherein the P-polarization reflectance of the mirror at the proximate angle of incidence $\theta_p$ is approximated by $$R_P(\lambda)=R_0(\lambda)e^{-\alpha(\lambda)(\sec(\theta_P)-1)}.$$

10. The method of claim 9, wherein the value calculated for $\alpha(\lambda)$ is scaled, based upon an assessment of computed reflectance values with respect to measured reflectance values.

11. The method of claim 9, wherein $\alpha(\lambda)$ is approximated for the proximate angle of incidence based upon an assessment of values of $\alpha(\lambda)$ calculated for a plurality of reference angles of incidence.

12. The method of claim 9, wherein $\alpha(\lambda)$ is approximated for the proximate angle of incidents based upon an average of values of $\alpha(\lambda)$ calculated for a plurality or reference angles of incidence.

13. The method of claim 9, wherein $\alpha(\lambda)$ is approximated for the proximate angle of incidence based upon an equation fitted to values of $\alpha(\lambda)$ calculated for a plurality of reference angles of incidence.

14. The method of claim 9, wherein steps (a), (b) and (c) are repeated at a plurality of wavelengths of incident light.

15. The method of claim 9, wherein, for a given α, α(λ) is assumed to be constant for a range of angles of incidence.

16. The method of claim 15, wherein the range of angles of incidence for which α(λ) is considered constant is based upon an assessment of values of α(λ) calculated for a plurality of reference angles of incidence.

17. The method of claim 16, wherein the assessment of values of α(λ) is a statistical assessment.

18. The method of claim 8,
wherein the S-polarization reflectance of the mirror at the proximate angle of incidence $\theta_p$ is approximated by $$R_S(\lambda) = R_0(\lambda) e^{-\alpha(\lambda)(cos(\theta)-1)}.$$

19. The method of claim 18 wherein α(λ) is approximated for the proximate angle of incidence based upon an average of values of α(λ) calculated for a plurality of reference angles of incidence.

20. The method of claim 18, wherein α(λ) is approximated for the proximate angle of incidence based upon an equation fitted to values of α(λ) calculated for a plurality of reference angles of incidence.

21. The method of claim 18, wherein steps (a), (b) and (c) are repeated at a plurality of wavelengths of incident light.

22. An apparatus for determining the reflectance of a mirror as a function of angle of incidence, comprising;
a detector that measures an S-polarization reflectance and a P-polarization reflectance of light reflected from a mirror at a reference angle of incidence; and
a processor that computes an approximation of at least one of the S-polarization reflectance and the P-polarization reflectance at a proximate angle of incidence other than the reference angle of incidence from the measured S-polarization and P-polarization reflectances.

23. The apparatus of claim 22, wherein the processor computes an approximation of at least one of the S-polarization reflectance and the P-polarization reflectance over a range of angles of incidence from the measured S-polarization and P-polarization reflectances.

24. The apparatus of claim 22, wherein the detector measures S-polarization and P-polarization reflectance values for the mirror at the reference angle at a plurality of wavelengths of incident light, and wherein said processor computes an approximation of at least one of the S-polarization reflectance and the P-polarization reflectance at the proximate angle of incidence from the S-polarization and P-polarization reflectances measured at the reference angle of incidence at the plurality of wavelengths of incident light.

25. The apparatus of claim 22, wherein the processor corrects measurements of a signal received from the detector using at least one of the S-polarization reflectance and the P-polarization reflectance computed at the proximate angle of incidence.

26. The apparatus of claim 22, wherein the processor compares a calculated reflectance value calculated for the reference angle of incidence to at least one measured reflectance value measured at the reference angle of incidence to determine a scalar value that is applied to reflectance values calculated for the reference angle of incidence for other wavelengths.

27. The apparatus of claim 22, wherein the processor uses the S-polarization reference of the mirror measured at the reference angle of incidence as an approximation of the P-polarization reflectance at normal incidence.

28. The apparatus of claim 27, wherein the processor computes a value of α(λ) determined by $$\alpha(\lambda) = \frac{\ln[R_P(\lambda)/R_0(\lambda)]}{1 - \sec(\theta_R)};$$

wherein $\theta_R$ is the reference angle of incidence, $R_p(\lambda)$ is the P-polarization reflectance measured at the reference angle of incidence $\theta_R$ at a wavelength λ, and $R_0(\lambda)$ is the P-polarization reflectance at normal incidence approximated by the S-polarization reflectance measured at the reference angle or incidence $\theta_R$.

29. The apparatus of claim 28,
wherein the processor approximates P-polarization reflectance of the mirror at the proximate angle of incidence $\theta_p$ as $$R_p(\lambda) = R_0(\lambda) e^{-\alpha(\lambda)sec(\theta_p)-1)}.$$

30. The apparatus of claim 29, wherein the processor scales the value calculated for α(λ) based upon an assessments of computed reflectance values with respect to measured reflectance values.

31. The apparatus of claim 29, wherein the processor approximates α(λ) for the proximate angle of incidence based upon an assessment of values of α(λ) calculated for a plurality of reference angles of incidence.

32. The apparatus of claim 29, wherein the processor approximates α(λ) for the proximate angle of incidence based upon an average of values of α(λ) calculated for a plurality of reference angles of incidence.

33. The apparatus of claim 29, wherein the processor approximates α(λ) for the proximate angle of incidence based upon an equation fitted to values of α(λ) calculated for a plurality of reference angles of incidence.

34. The apparatus of claim 29, wherein the processor computes an approximation of at least one of the S-polarization reflectance and the P-polarization reflectance over a range of angles of incidence from the S-polarization and P-polarization reflectances measured at the reference angle of incidence for a plurality of wavelengths of incident light.

35. The apparatus of claim 28,
wherein the processor approximates S-polarization reflectance of the mirror at a proximate agile of incidence $\theta_p$ as $$R_s(\lambda) = R_o(\lambda) e^{-\alpha(\lambda)(cos(\theta)-1)}.$$

36. An apparatus for determining the reflectance of a mirror as a function of angle of incidence comprising:
a mirror that receives and reflects incident light;
a controller that controls positioning of the mirror;
a detector that measures an S-polarization reflectance and a P-polarization reflectance of light reflected from a mirror at a reference angle of incidence; and
a processor that computes an approximation of at least one of the S-polarization reflectance and the P-polarization reflectance at a proximate angle of incidence other than the reference angle of incidence from the measure S-polarization and P-polarization reflectances.

\* \* \* \* \*